US010466174B2

(12) United States Patent
Glacer et al.

(10) Patent No.: US 10,466,174 B2
(45) Date of Patent: Nov. 5, 2019

(54) GAS ANALYZER INCLUDING A RADIATION SOURCE COMPRISING A BLACK-BODY RADIATOR WITH AT LEAST ONE THROUGH-HOLE AND A COLLIMATOR

(71) Applicant: Infineon Technologies AG, Neubiberg (DE)

(72) Inventors: Christoph Glacer, Munich (DE); Alfons Dehe, Reutlingen (DE); David Tumpold, Kirchheim (DE); Gueclue Onaran, Munich (DE)

(73) Assignee: Infineon Technologies AG, Neubiberg (DE)

( * ) Notice: Subject to any disclaimer, the term of this patent is extended or adjusted under 35 U.S.C. 154(b) by 177 days.

(21) Appl. No.: 15/376,738

(22) Filed: Dec. 13, 2016

(65) Prior Publication Data

US 2018/0164215 A1    Jun. 14, 2018

(51) Int. Cl.
| | | |
|---|---|---|
| *G01N 21/64* | (2006.01) | |
| *G01N 21/84* | (2006.01) | |
| *G01N 21/17* | (2006.01) | |
| *G01N 21/3504* | (2014.01) | |

(52) U.S. Cl.
CPC ..... *G01N 21/6404* (2013.01); *G01N 21/1702* (2013.01); *G01N 21/3504* (2013.01); *G01N 21/84* (2013.01); *G01N 2021/1704* (2013.01); *G01N 2201/0633* (2013.01)

(58) Field of Classification Search
CPC ............... G01N 21/6404; G01N 21/84; G01N 2201/0633; G01N 2021/6463; G01N 2021/6471; G01N 21/39; G01N 21/3504; G01N 21/1702; G01N 2021/1704; G01J 3/02; G01J 3/4406; G01J 3/021; G01J 3/10; G01J 3/443; G01J 3/4412; G01J 5/0803

See application file for complete search history.

(56) References Cited

U.S. PATENT DOCUMENTS

| | | | | | |
|---|---|---|---|---|---|
| 3,588,496 | A | * | 6/1971 | Snowman | G01N 21/031 250/343 |
| 4,787,750 | A | * | 11/1988 | Nelson | G01N 21/3504 356/437 |
| 5,747,820 | A | * | 5/1998 | Karlsson | G01J 3/108 250/493.1 |

(Continued)

FOREIGN PATENT DOCUMENTS

WO        WO 9309422 A1 *  5/1993 .............. G01J 3/26

*Primary Examiner* — Georgia Y Epps
*Assistant Examiner* — Jennifer D Bennett
(74) *Attorney, Agent, or Firm* — Viering, Jentschura & Partner MBB

(57) ABSTRACT

A gas analyzer may include: a gas chamber configured to receive a gas to be analyzed therein, a radiation source configured to emit electromagnetic radiation into the gas chamber, the electromagnetic radiation being adapted to selectively excite gas molecules of a specific type that is to be detected in the gas received in the gas chamber, a collimator configured to collimate the electromagnetic radiation emitted by the radiation source, and a sensor configured to detect a physical quantity indicative of a degree of interaction between the electromagnetic radiation emitted by the radiation source and the gas to be analyzed.

23 Claims, 7 Drawing Sheets

(56) References Cited

U.S. PATENT DOCUMENTS

| | | | | |
|---|---|---|---|---|
| 6,599,253 | B1* | 7/2003 | Baum | A61B 5/0813 |
| | | | | 356/303 |
| 8,415,626 | B1* | 4/2013 | Wong | G01J 5/045 |
| | | | | 250/340 |
| 8,729,475 | B1* | 5/2014 | Wong | G01N 21/3504 |
| | | | | 250/343 |
| 9,551,829 | B2* | 1/2017 | Brun | G01N 21/1702 |
| 2003/0177814 | A1* | 9/2003 | Weckstrom | G01N 21/3504 |
| | | | | 73/25.01 |
| 2003/0209669 | A1* | 11/2003 | Chou | G01N 21/3504 |
| | | | | 250/343 |
| 2005/0214167 | A1* | 9/2005 | Archibald | B01L 3/5085 |
| | | | | 422/68.1 |
| 2006/0123884 | A1* | 6/2006 | Selker | G01N 21/1702 |
| | | | | 73/24.02 |
| 2009/0268204 | A1* | 10/2009 | Tkachuk | G01N 21/3504 |
| | | | | 356/437 |
| 2010/0118301 | A1* | 5/2010 | Vondras | G01J 3/10 |
| | | | | 356/318 |
| 2013/0062710 | A1 | 3/2013 | Dehe | |
| 2015/0101395 | A1* | 4/2015 | Dehe | G01N 29/2418 |
| | | | | 73/24.02 |
| 2016/0356700 | A1* | 12/2016 | Rouxel | G01N 29/2418 |

* cited by examiner

GAS ANALYZER INCLUDING A RADIATION SOURCE COMPRISING A BLACK-BODY RADIATOR WITH AT LEAST ONE THROUGH-HOLE AND A COLLIMATOR

TECHNICAL FIELD

Various embodiments relate generally to a gas analyzer.

BACKGROUND

Gas analyzers, either configured as photoacoustic gas detectors or as non-dispersive radiation spectrometers, provide a simple way of analyzing the composition of gases. Since the analysis of the composition of ambient air, e.g., due to pollution, is becoming increasingly important, it is desirable to provide a gas analyzer with a simple structure capable of measuring the composition of gases in a highly efficient manner.

SUMMARY

According to various embodiments of the present disclosure a gas analyzer is provided. The gas analyzer may include: a gas chamber configured to receive a gas to be analyzed therein, a radiation source configured to emit electromagnetic radiation into the gas chamber, the electromagnetic radiation being adapted to selectively excite gas molecules of a specific type that is to be detected in the gas received in the gas chamber, a collimator configured to collimate the electromagnetic radiation emitted by the radiation source, and a sensor configured to detect a physical quantity indicative of a degree of interaction between the electromagnetic radiation emitted by the radiation source and the gas to be analyzed.

BRIEF DESCRIPTION OF THE DRAWINGS

In the drawings, like reference characters generally refer to the same parts throughout the different views. The drawings are not necessarily to scale, emphasis instead generally being placed upon illustrating the principles of the invention. In the following description, various embodiments of the invention are described with reference to the following drawings, in which.

DESCRIPTION

The following detailed description refers to the accompanying drawings that show, by way of illustration, specific details and embodiments in which the invention may be practiced.

The word "exemplary" is used herein to mean "serving as an example, instance, or illustration". Any embodiment or design described herein as "exemplary" is not necessarily to be construed as preferred or advantageous over other embodiments or designs.

The word "collimated electromagnetic radiation" used herein means electromagnetic radiation with a low degree of dispersion as it propagates.

The word "collimator" used herein is a device configured to narrow a beam of electromagnetic radiation.

The word "optical axis" used herein is an imaginary line that defines a path along which electromagnetic radiation propagates through a system up to first approximation.

The word "focal point of a collimator" refers to a characteristic point on the optical axis of a collimator to which parallel rays of electromagnetic radiation converge or from which they diverge to parallel rays after being refracted or reflected by the collimator.

Figure 1:
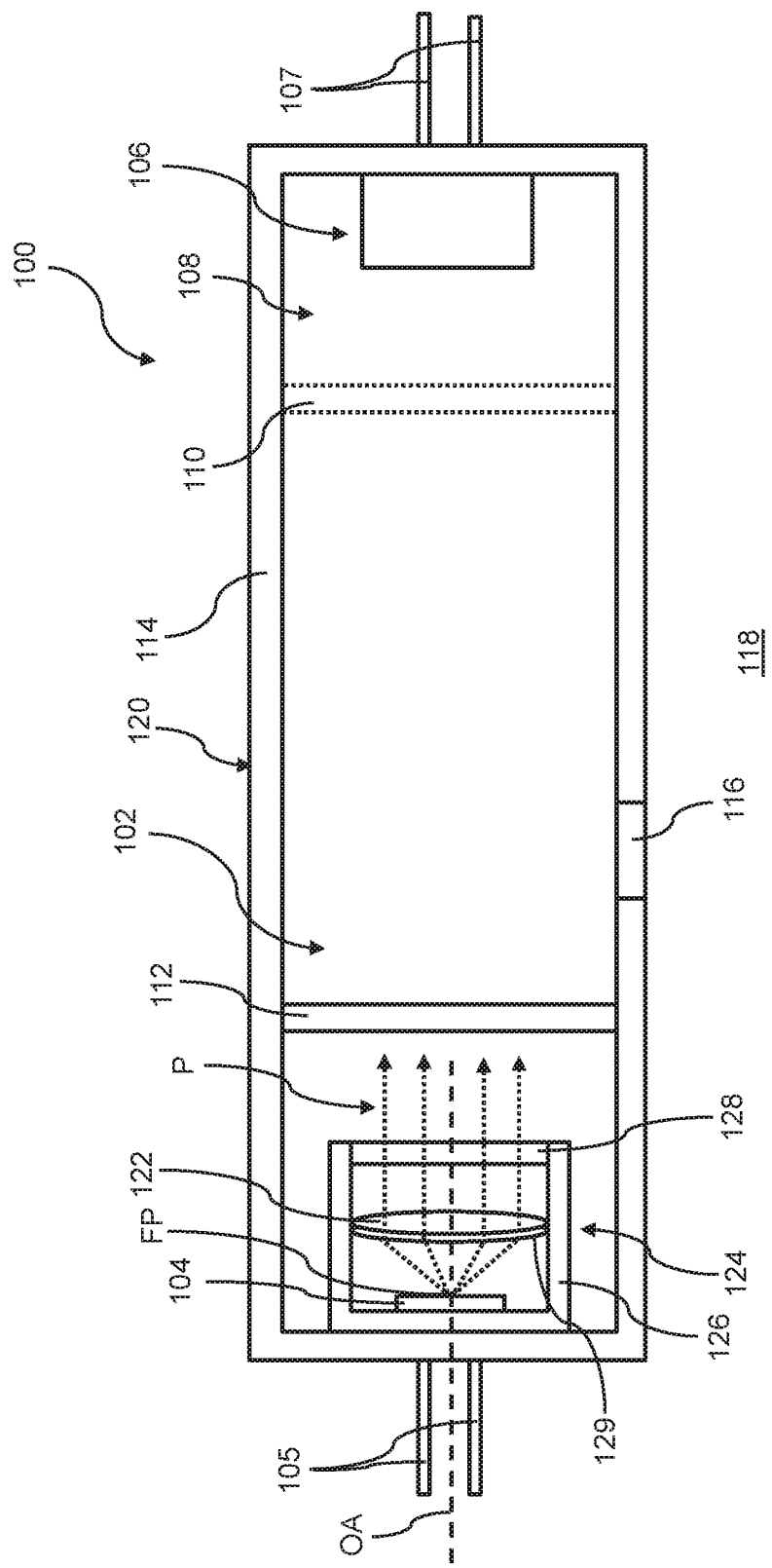
FIG. 1 is a schematic view of a gas analyzer including a source unit.

FIG. 1 is a schematic view of a gas analyzer 100. The gas analyzer 100 may include a gas chamber 102 configured to receive a gas to be analyzed therein, a radiation source 104 configured to emit electromagnetic radiation into the gas chamber 102, the electromagnetic radiation being adapted to selectively excite gas molecules of a specific type that is to be detected in the gas received in the gas chamber 102, and a sensor 106 configured to detect a physical quantity indicative of a degree of interaction between the electromagnetic radiation emitted by the radiation source 104 and the gas to be analyzed. The degree of interaction between the electromagnetic radiation emitted by the radiation source 104 and the gas to be analyzed may be indicative of the concentration of gas molecules of a specific type that is to be detected in the gas received in the gas chamber 102.

The gas analyzer 100 may be configured as a photoacoustic gas analyzer. In a such configured gas analyzer, the physical quantity indicative of the degree of interaction between the electromagnetic radiation emitted by the radiation source 104 and the gas to be analyzed are acoustic waves generated as a result of the excitation of gas molecules of the type that is to be detected in the gas received in the gas chamber 102 by the electromagnetic radiation emitted by the radiation source 104. The working principle of a photoacoustic gas analyzer will be outlined in the following.

In a photoacoustic gas analyzer, the radiation source 104 is configured to emit electromagnetic radiation in a time-varying fashion, e.g., periodically, i.e. with a time-varying intensity. The electromagnetic radiation emitted by the radiation source 104 may be adapted to induce specific atomic and/or molecular transitions in gas molecules of the type that is to be detected in the gas received in the gas chamber 102 and/or to excite various vibrational and/or rotational modes of said gas molecules. During the subsequent de-excitation of the thus excited gas molecules, heat is generated leading to a local expansion of the gas received in the gas chamber 102 causing a positive pressure pulse.

The excessive heat generated in this way is subsequently dissipated to a heat sink leading to a contraction of the gas causing a negative pressure pulse. A heat sink may be provided by a holder that is in physical contact with the photoacoustic gas analyzer 100.

Since the electromagnetic radiation is emitted in a time-varying fashion, the gas molecules of the type that is to be detected are excited in a time-varying fashion, e.g. periodically. In this way, a time-varying, e.g. periodic, pressure fluctuation is generated in the gas received in the gas chamber 102 containing the gas molecules of the type that is to be detected. Hence, acoustic waves are generated in this way. In a photoacoustic gas analyzer, the sensor 106 may include or may be configured as an acoustic-wave detector configured to detect acoustic waves generated by the interaction of the electromagnetic radiation emitted by the radiation source 104 with gas molecules of the type that is to be detected in the gas chamber 102.

The acoustic-wave detector 106 may be positioned inside of the gas chamber 102. In a such configured photoacoustic gas analyzer 100, the sensor response increases with an increasing concentration of the gas molecules of interest, i.e. of the gas molecules of the type that is to be detected. A photoacoustic gas analyzer 100 of this kind is referred to in this specification as a photoacoustic gas analyzer 100 of the direct detection type.

Alternatively, the photoacoustic gas analyzer 100 may be configured as a photoacoustic gas analyzer of the differential detection type, meaning that the acoustic-wave detector 106 is not positioned inside of the gas chamber 102, but in a reference-gas chamber 108 gas-tightly separated from the gas chamber 102 by a window 110 that is transparent for the electromagnetic radiation emitted by the radiation source 104. In the reference-gas chamber 108, a reference gas with a well-defined composition including gas molecules of interest is received.

In a photoacoustic gas analyzer 100 of the differential detection type electromagnetic radiation emitted by the radiation source 104 passes through the gas chamber 102 and selectively interacts with gas molecules of interest. By means of the selective interaction with the molecules of interest, the intensity of the electromagnetic radiation is attenuated depending on the concentration of the molecules of interest in the gas to be analyzed in the gas chamber 102, meaning that the attenuation increases with increasing concentration of the molecules of interest. Consequently, the attenuation of the electromagnetic radiation is indicative of the concentration of the gas molecules of interest. After passing through the gas chamber 102, the electromagnetic radiation enters the reference-gas chamber 108 through the window 110 and selectively excites gas molecules of interest in the reference gas. The more the electromagnetic radiation is attenuated in the gas chamber 102 the lower is its intensity in the reference-gas chamber 108 and the lower is the response of the acoustic-wave detector 106. Consequently, in a photoacoustic gas analyzer 100 of the differential detection type, the response of the acoustic-wave detector 106 decreases with increasing concentration of the gas molecules of interest in the gas chamber 102. From a comparison with a calibrated maximum response of the acoustic-wave sensor 106 in the case of a vanishing concentration of the molecules of interest in the gas chamber 102, the actual concentration of the molecules of interest in the gas chamber 102 can be determined.

The radiation source 104 may be configured to emit electromagnetic radiation in the infrared and/or in the visible and/or in the ultraviolet frequency range. Infrared light is suitable for exciting vibrational molecular modes. By way of example, infrared light with a wavelength ranging from about 4.170 to about 4.370 µm and from about 14 to about 16 µm is suitable for exciting vibrational modes of $CO_2$ molecules.

The radiation source 104 may include at least one of a group including a black-body radiator, a photodiode, and a laser. Power supply lines 105 of a such configured radiation source 104 are shown in FIG. 1.

A black-body radiator is configured to emit electromagnetic radiation according to Planck's law, meaning that its radiation spectrum is determined by its temperature, not by its shape or composition. The radiation source 104 may include a black-body radiator configured as an electrically heatable body such as a membrane. In operation, the electrically heatable body may be electrically heated up to temperatures higher than 450° C.

The acoustic-wave detector 106 may include or may be configured as a capacitive acoustic-wave detector having two membranes spaced apart from each other and defining a capacitor therebetween. One of the membranes may be fixed and the respective other one may be displaceable by acoustic waves to be detected. A displacement of the displaceable membrane may be indicative of characteristics of the acoustic waves to be detected and may induce a change of the capacitance of the capacitor that can be detected by a suitable read-out circuit providing an electrical signal indicative of characteristics of the acoustic waves to be detected such as of the acoustic pressure.

Additionally or alternatively, the acoustic-wave sensor 106 may include or may be configured as a piezoelectric acoustic-wave sensor having a piezoelectric thin film that is deformable by acoustic waves to be detected. A deformation of the piezoelectric thin film may generate an electric voltage therein that is indicative of characteristics of acoustic waves to be detected. The induced electric voltage may be read out by a suitable read-out circuit providing an electric signal indicative of characteristics of the acoustic waves to be detected such as of the acoustic pressure.

In FIG. 1, reference numeral 107 denotes signal and/or power supply lines of the sensor 106. The sensor 106 may be connected to a processing unit configured, e.g., as an application specific integrated circuit (ASIC) or as a microprocessor, and adapted to determine the concentration of gas molecules of interest in the gas chamber 102 from signals received from the sensor 106.

Alternatively, the gas analyzer 100 may be configured as a nondispersive radiation detector, in particular as a nondispersive infrared detector (NDIR). In a gas analyzer of this kind, the sensor 106 is configured as an electromagnetic radiation sensor such as an infrared sensor, and the physical quantity indicative of the degree of interaction between the electromagnetic radiation emitted by the radiation source 104 and the gas molecules of interest is the intensity of the electromagnetic radiation detected by the radiation sensor 106. The higher the concentration of the molecules of interest in the gas received in the gas chamber 102 is, the lower will be the intensity of the electromagnetic radiation detected by the sensor 106. From a comparison of the detected intensity with a calibrated maximum intensity in case of a vanishing concentration of the molecules of interest in the gas chamber 102, the actual concentration of the molecules of interest in the gas chamber 102 can be determined.

The gas analyzer 100 may further include a window 112 transparent for electromagnetic radiation emitted by the radiation source 104 and positioned between the radiation source 104 and the gas chamber 102.

The window 112 may be configured as a filter. By means of the filter 112, the spectrum of the radiation emitted by the radiation source 104 may be limited to a narrow energy range including a single excitation energy to make sure that only molecules of a single type are excited at a given time, i.e. that molecules of types different from the type which is to be detected in the gas received in the gas chamber 102 are not unintentionally also excited. In this way, the measurement selectivity can be improved as compared to a gas analyzer without a filter.

In case only a single type of gas molecules is to be detected in the gas received in the gas chamber 102, the filter 112 may be configured to have fixed transmission characteristics. Alternatively, in case gas molecules of different types having mutually different excitation energies are to be detected in the gas to be analyzed, a tunable filter 112 with tunable transmission characteristics may be employed. In operation, the transmission characteristics of the filter 112 may be varied to excite gas molecules of different types. The filter 112 may include or may be configured as a plasmonic filter and/or a Fabry-Pérot interferometer such as a Fabry-Pérot etalon.

The gas analyzer may be used for monitoring the composition of ambient air, e.g., for determining the content of $CO_2$ and/or of toxic gases such as of CO in ambient air. Methane and/or water molecules (humidity) in ambient air may also be detected in this way. Alternatively or additionally, the gas analyzer 100 may be configured and used as a breath analyzer to measure the content of alcohol and/or acetone which is indicative of the blood glucose level.

As indicated in FIG. 1, the gas chamber 102 may be delimited by a gas chamber wall 114. A through hole 116 serving as a gas inlet and/or outlet may be provided in the gas chamber wall 114. The through hole 116 may be at least temporarily or permanently open. In this way, the gas chamber 102 may be temporarily or even permanently in gas flow communication with the exterior 118 of the gas analyzer 100. A gas exchange between the gas chamber 102 and the exterior 118 of the gas analyzer 100 by diffusion may be provided in this way such that the composition of ambient air can be monitored by means of the gas analyzer 100.

A high efficiency of the excitation of gas molecules of interest in the gas chamber 102 may be achieved by providing a reflector 120 on the gas chamber wall 114. The reflector 120 may have a reflectance in the infrared and/or in the visible and/or in the ultraviolet frequency range of at least 20% or of at least 50% or even of at least 80%.

A high excitation efficiency may also be provided by means of a collimator 122 configured to collimate electromagnetic radiation emitted by the radiation source 104.

By means of a collimation of the beam, a higher amount of the electromagnetic radiation may be directed into the gas chamber 102 as compared to a gas analyzer 100 without a collimator. In this way, the intensity of the electromagnetic radiation in the gas chamber 102 can be accordingly enhanced. Consequently, gas molecules of interest can be more efficiently excited as compared to a gas analyzer 100 without a collimator 122. In this way, the sensitivity of the gas analyzer 100 can be enhanced.

As indicated in FIG. 1, the collimator 122 may be configured as a convex lens, in particular as a biconvex lens. The radiation source 104 may be positioned in or may overlap a focal point FP of the biconvex lens 122 on a side of the biconvex lens 122 opposite to the gas chamber 102. In this way, the beam of electromagnetic radiation emitted by the radiation source 104 may be parallelized by the biconvex lens 122, meaning that rays of electromagnetic radiation emitted by the radiation source 104 are converted into parallel rays by the collimator 122. In this way, the radiation amount emitted towards the interior surface of the gas chamber wall 114 is minimized, thereby minimizing absorption losses in the gas chamber wall 114. In addition, a well-defined angle of incidence between the parallel beam of electromagnetic radiation and the surface of the filter 112 facing the radiation source 104 may be ensured, thereby reducing a decrease of the intensity of the beam of electromagnetic radiation due to reflection, in particular total reflection, at said surface of the filter 112. Consequently, a highly efficient excitation of gas molecules of interest in the gas chamber 102 may be ensured. The parallel radiation beam is denoted by the reference character P in FIG. 1.

The collimator 122 may have an optical axis OA intersecting the collimator 122 and/or the radiation source 104.

As indicated in FIG. 1, the radiation source 104 and the collimator 122 may be integrated into a source unit 124. The source unit 124 may include a holder 126 carrying the radiation source 104 and the collimator 122. The source unit 124 may further include a source unit filter 128 separated from the collimator 122 and supported by the holder 126. The source unit filter 128 may be configured as a filter with fixed transmission characteristics or as a tunable filter the transmission characteristics of which are tunable.

As further shown in FIG. 1, a collimator filter 129 in physical contact with the collimator 122 may be additionally or alternatively provided. By way of example, the collimator filter 129 may be configured as a layer deposited on a surface of the biconvex lens 122, e.g., on a surface of the biconvex lens 122 facing the radiation source 104. Alternatively, a filter layer may be provided on a surface of the biconvex lens 122 opposite to the radiation source 104. A biconvex lens 122 equipped with filter layers on both surfaces thereof is also conceivable.

The source unit 124 may be provided as a pre-assembled unit. In this way, the gas analyzer 100 may be manufactured in a simple way.

Figure 2:
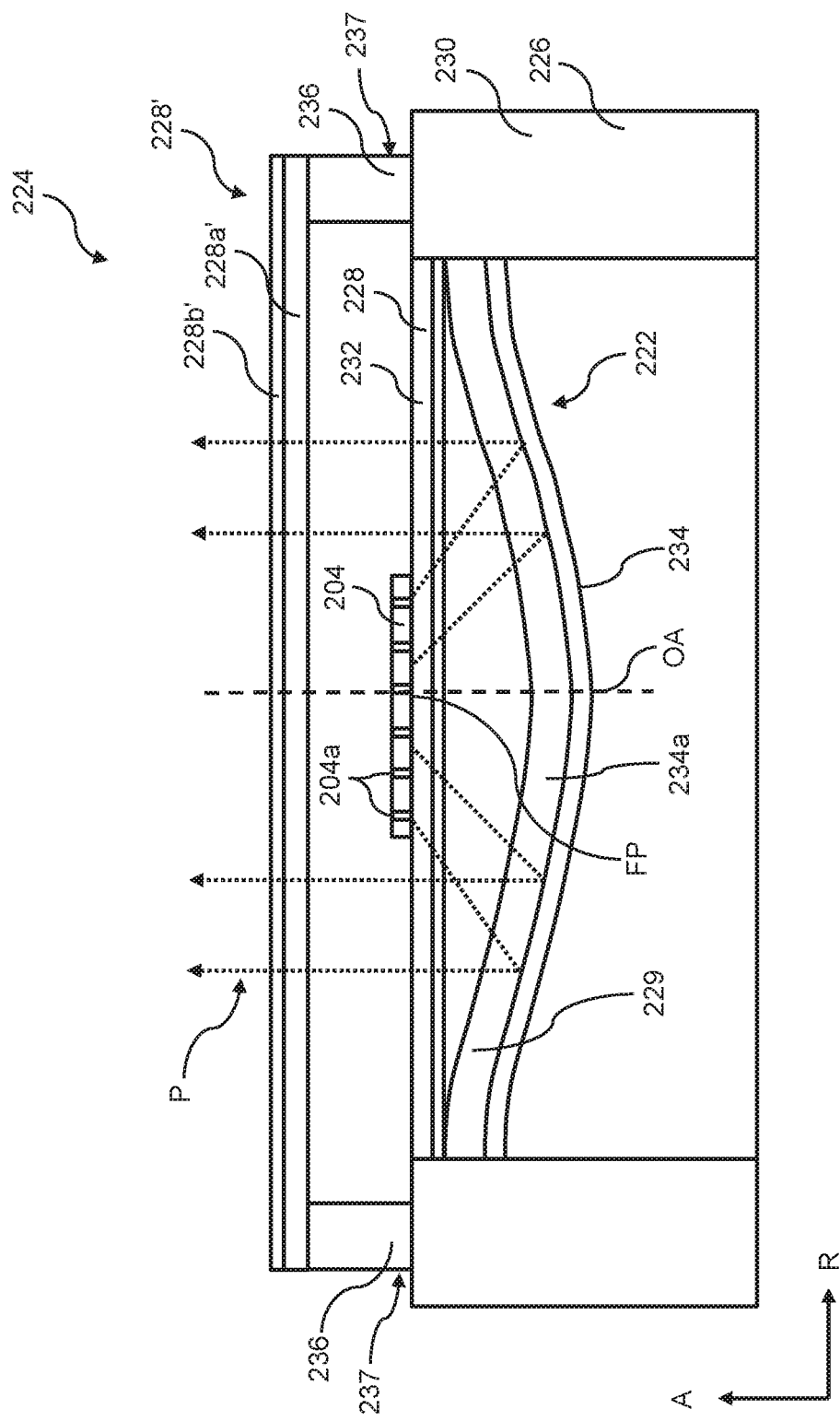
FIG. 2 is a schematic view of a modified source unit.

FIG. 2 shows a modified source unit in more detail as compared to the source unit 124 depicted in FIG. 1. In FIG. 2, parts corresponding to parts of the source unit 124 of FIG. 1 are denoted by the same reference numerals, however, enhanced by the number 100.

The source unit 224 shown in FIG. 2 may include a holder 226 including a base portion 230 and a carrier 232 coupled to the base portion 230 and supporting the radiation source 204. The carrier 232 may be transparent for electromagnetic radiation emitted by the radiation source 204. Additionally, the carrier 232 may be configured as a source unit filter 228 configured to selectively transmit electromagnetic radiation emitted by the radiation source 204.

As shown in FIG. 2, the base portion 230 of the holder 226 may have a substantially annular shape. The carrier 232 may be configured as a membrane coupled to a radially inner circumferential part of the base portion 230 and may be optionally made of a material having a low thermal conductivity of, e.g., less than 5 W/(m·K). In this way, the radiation source 204 may be thermally decoupled from the holder 226, and, hence, from the gas to be analyzed.

In FIG. 2 the radial and the axial directions of the source unit 224 are denoted by the reference characters R and A, respectively.

The source unit 224 may further include a collimator 222. The collimator 222 may include or may be configured as a concave mirror 234. The radiation source 204 may be positioned in or may overlap a focal point FP of the concave mirror 234. In this way, radiation reflected by the mirror 234 may be parallelized. The parallelized radiation beam is denoted by the reference character P in FIG. 2. The mirror 234 may be coupled to a radially inner part of the base portion 230.

The collimator 222 may have an optical axis OA intersecting the collimator 222 and/or the radiation source 204.

The mirror 234 may be in physical contact with a transparent layer 234a arranged on a side of the mirror 234 facing the radiation source 204 and being configured to transmit electromagnetic radiation emitted by the radiation source 204. The mirror 234 may be configured as a metallic layer. The transparent layer 234a may be configured as a collimator filter 229, i.e., as a filter that is in physical contact with the collimator 222.

Alternatively, the collimator 222 may be configured as a Bragg reflector, i.e. as a reflector including a plurality of transparent layers with mutually different refractive indices. In a reflector of this kind, a metallic reflective layer may be omitted.

In case the radiation source 204 is configured as a black-body radiator, the radiation source 204 may include at least one or a plurality of perforations 204a in order to reduce the degree of absorption of radiation reflected by the collimator 222 by the radiation source 204 itself as compared to an identical radiation source without perforations. In this way, electromagnetic radiation reflected by the collimator 222 may pass through the radiation source 204, thereby enhancing the output of electromagnetic radiation as compared to a radiation source 204 without perforations 204a.

The source unit 224 may further include a source unit filter 228' different from the carrier 232 and positioned on a side of the radiation source 204 opposite to the collimator 222. The source unit filter 228' may be supported by a plurality of posts 236 positioned on an axial side of the holder 226. The source unit filter 228' may include a plurality of filter layers 228a', 228b'. The filter layers 228a', 228b' may have mutually different well-defined transmission characteristics in respective narrow frequency bands. Consequently, by integrating the filter layers 228a' and 228b' to a single filter, a filter with well-defined transmission characteristics in a wider frequency range as compared to a single layer may be provided in this way.

In an exemplary embodiment, one of the layers 228a', 228b' may be formed of $SiO_2$ and the respective other one of polycrystalline silicon. Although in FIG. 2 the source unit filter 228' is shown to include only two layers 228a', 228b', it is understood that the number of layers may be varied as desired. In an exemplary embodiment, a source unit filter may include more than two alternating layers made of polycrystalline silicon and $SiO_2$, respectively.

The posts 236 may be coupled to the holder 226 and/or to the source unit filter 228' by gluing or anodic bonding. At least one of the posts 236 may be equipped with a reflector 237 on an outer surface thereof configured to reflect electromagnetic radiation emitted by the radiation source 204. In this way, a high electromagnetic radiation output may be ensured.

In the following, an exemplary method of manufacturing a collimator configured as a concave mirror will be described with reference to FIGS. 3A to 3G as well as with reference to the flowchart shown in FIG. 4.

Figure 3A:
FIGS. 3A to 3G illustrate an exemplary method of manufacturing a collimator of the source unit shown in FIG. 2.
Figure 3B:
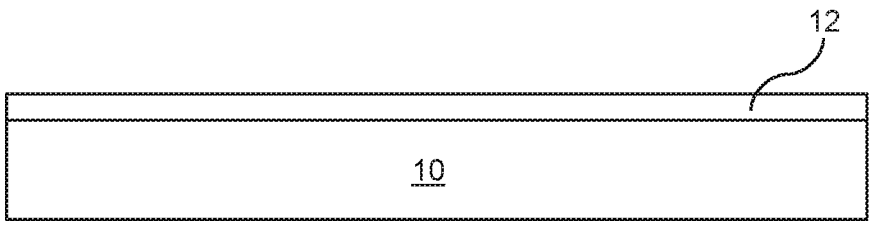
Figure 3C:
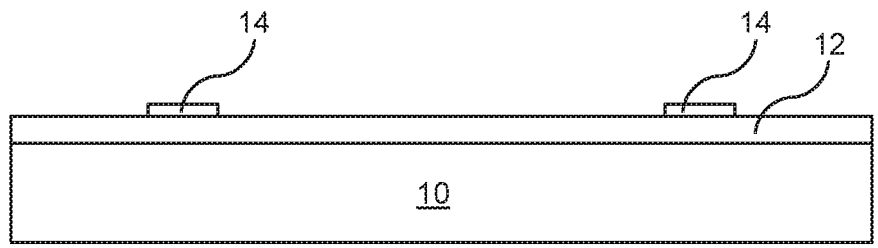
Figure 3D:
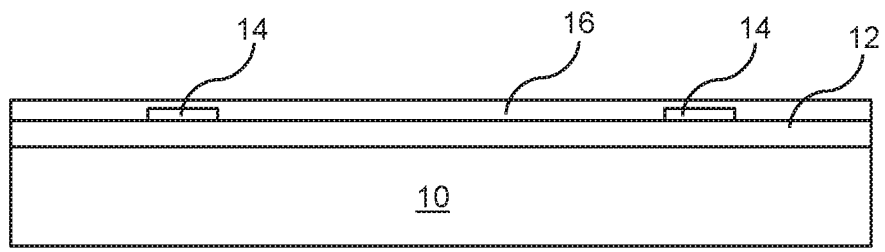
Figure 3E:
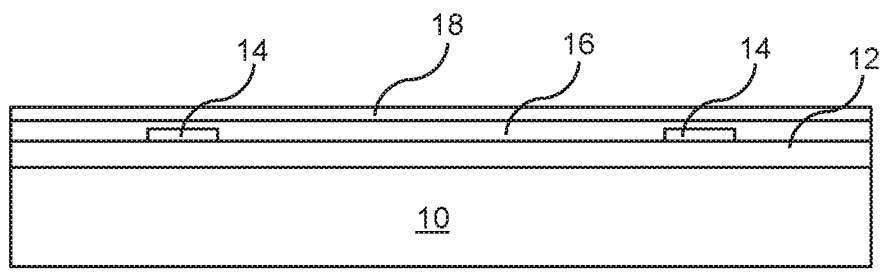
Figure 3F:
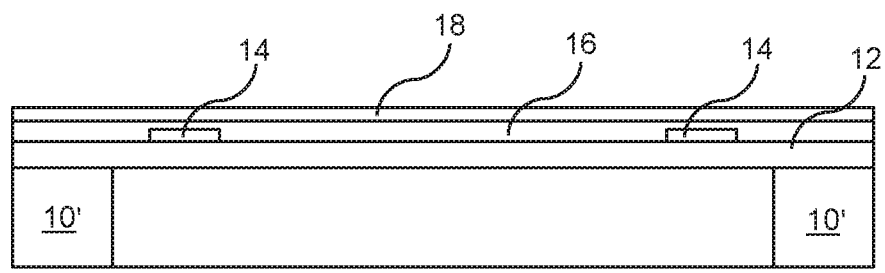
Figure 3G:
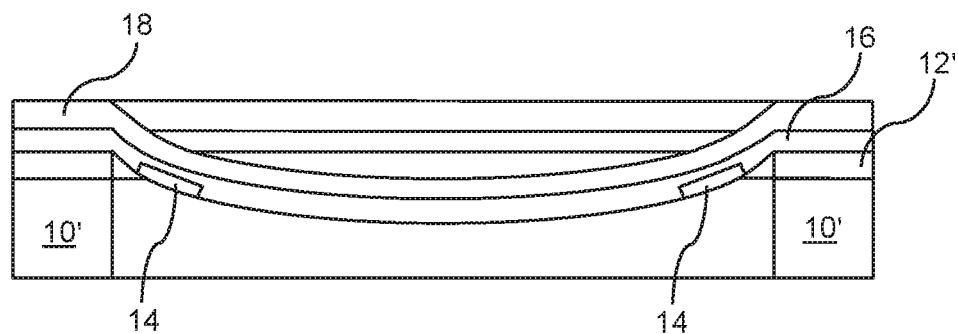
Figure 4:
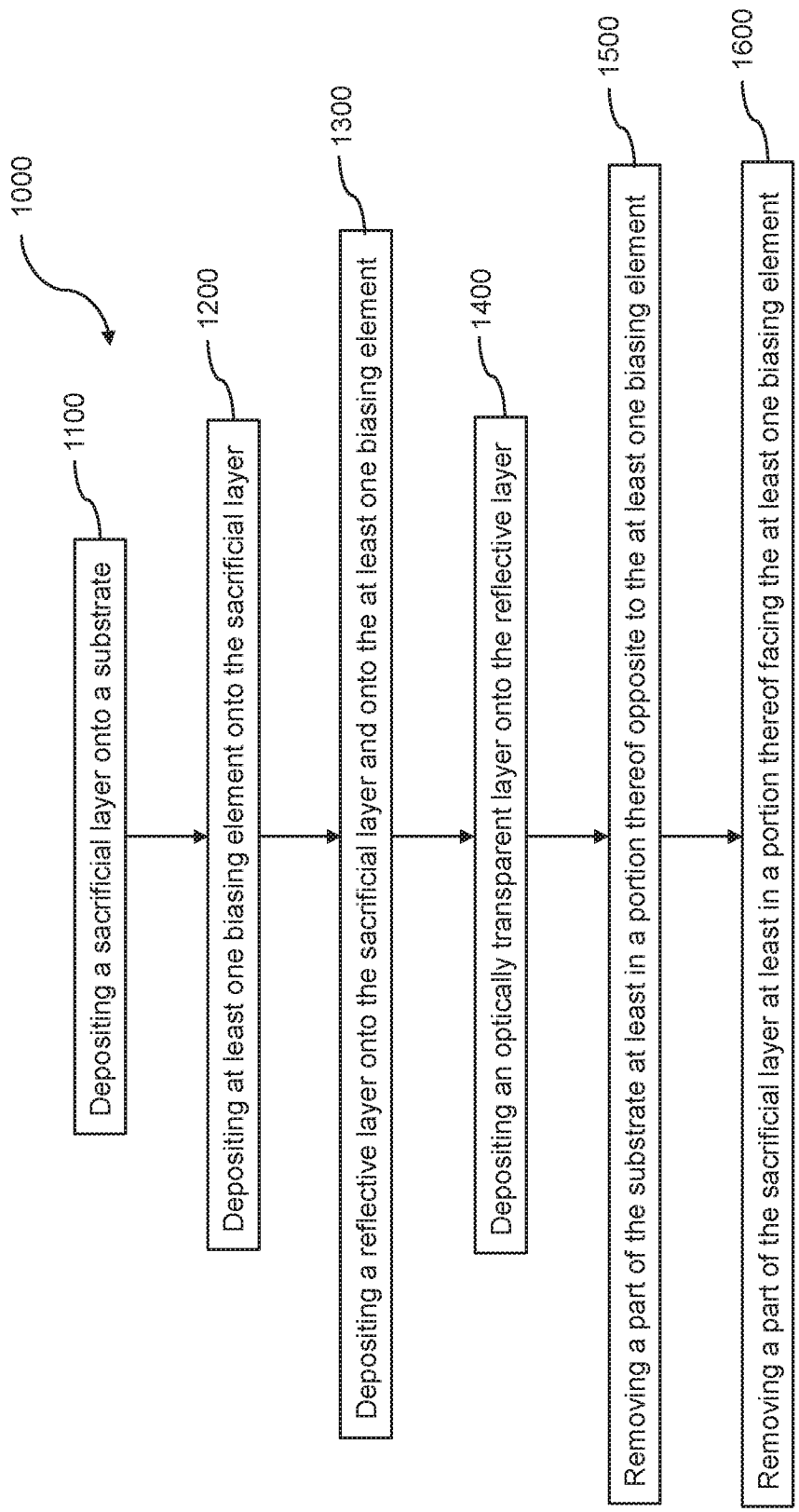
FIG. 4 is a flowchart of the exemplary method illustrated in FIGS. 3A to 3G.

The exemplary method 1000 may include:

Depositing a sacrificial layer 12, e.g. a $SiO_2$ layer, onto a substrate 10, e.g. a silicon substrate (FIGS. 3A, 3B, and S1100 in FIG. 4);

Depositing at least one biasing element 14 onto the sacrificial layer 12 (FIG. 3C and S1200 in FIG. 4);

Depositing a reflective layer 16 onto the sacrificial layer 12 and onto the at least one biasing element 14 (FIG. 3D and S1300 in FIG. 4);

Depositing an optically transparent layer 18 onto the reflective layer 16 (FIG. 3E and S1400 in FIG. 4);

Removing a part of the substrate 10 at least in a portion thereof opposite to the at least one biasing element 14 (FIG. 3F and S1500 in FIG. 4); and Removing a part of the sacrificial layer 12 at least in a portion thereof facing the at least one biasing element 14 (FIG. 3G and S1600 in FIG. 4).

As shown in FIGS. 3C to 3G, a plurality of biasing elements 14 may be deposited onto a surface of the sacrificial layer 12 opposite to the substrate 10.

The at least one biasing element 14 is configured to exert a mechanical stress onto the reflective layer 16 and onto the optically transparent layer 18. This may be achieved by manufacturing the at least one biasing element 14 of a material with a higher or lower thermal expansion coefficient as compared to the respective thermal expansion coefficient of the material of the reflective layer 16 and/or of the optically transparent layer 18. The reflective layer 16 and the optically transparent layer 18 may be manufactured at elevated temperatures, i.e. at temperatures that are substantially higher than the temperatures in operation of a gas analyzer employing a collimator of this kind. In the course of a subsequent cooling down of the reflective layer 16, the optically transparent layer 18, and the at least one biasing element 14 a bending deflection of the reflective layer 16 and of the optically transparent layer 18 occurs due to the different thermal expansion characteristics.

In an exemplary embodiment, the optically transparent layer 16 may be formed of polycrystalline silicon and the at least one biasing element 14 may be formed of $Si_3N_4$. The part of the substrate 10 opposite to the at least one biasing element 14 may be removed by Deep Reactive Ion Etching (DRIE), e.g., in case the substrate 10 is made of silicon and the sacrificial layer 12 is made of $SiO_2$. In this case, the substrate 10 may be selectively etched by DRIE while the sacrificial layer 12 acts as an etch stop layer.

The etched substrate 10' may have, as indicated in FIGS. 3F and 3G, a substantially annular shape.

The sacrificial layer 12 may be subsequently removed, e.g., by HF etching. The etched sacrificial layer is denoted by the reference character 12' in FIG. 3G. Depending on the thickness of the sacrificial layer 12 and/or the thicknesses of the reflective layer 16 and the optically transparent layer 18 and/or the configuration of the biasing elements 14, the bending deflection of the reflective layer 16 and of the optically transparent layer 18 may occur only after removal of a part of the sacrificial layer 12 facing the at least one biasing element 14. The individual thicknesses of the sacrificial layer 12 and/or of the reflective layer 16 and/or of the optically transparent layer 18 may range from about 100 nm to about 1 μm.

The reflective layer 16 may be made of a metal such as of aluminum or gold.

The reflective layer 16 may act as the mirror 234 shown in FIG. 2, and the optically transparent layer 18 may act as the transparent layer 234a shown in FIG. 2.

As mentioned previously with respect to FIG. 2, the collimator 222 may be alternatively configured as a Bragg reflector. A collimator of this kind may be manufactured by depositing a plurality of alternating optically transparent layers with mutually different refractive indices, e.g., a plurality of alternating layers made of $SiO_2$ and polycrystalline silicon onto the reflective layer 16, or onto the sacrificial layer 12 and onto the at least one biasing element 14 without depositing a reflective layer. A bending deflection of the plurality of layers of the Bragg reflector may be achieved by the biasing elements 14 as discussed above.

Figure 5:
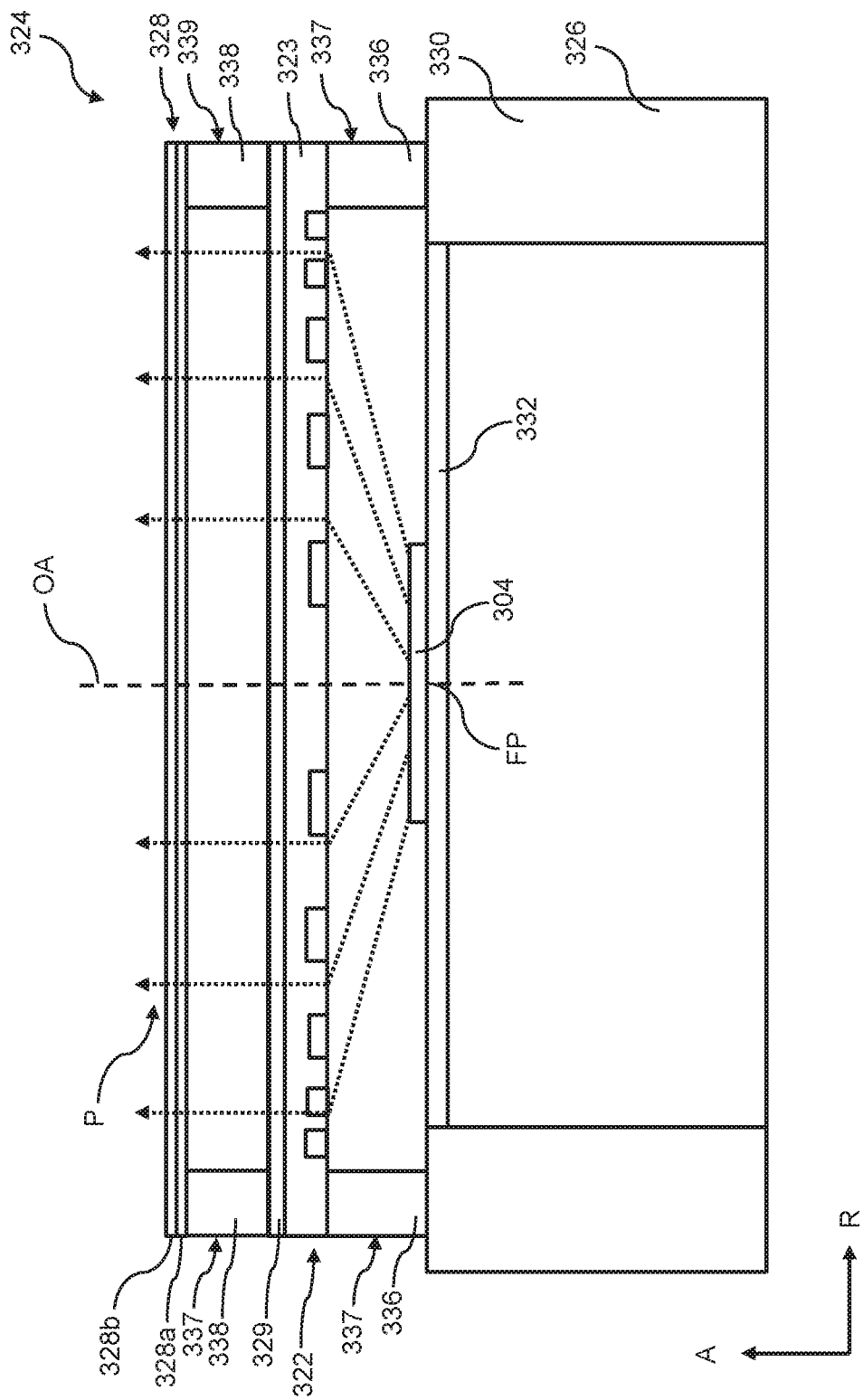
FIG. 5 is a schematic view of another modified source unit.

FIG. 5 shows a further modified source unit. In FIG. 5, parts corresponding to parts of the source unit 124 of FIG. 1 are denoted by the same reference numerals, however, enhanced by the number 200.

The source unit 324 shown in FIG. 5 may include a holder 326 including a base portion 330 and a carrier 332 coupled to the base portion 330 and supporting the radiation source 304.

As shown in FIG. 5, the base portion 330 of the holder 326 may have a substantially annular shape. The carrier 332 may be configured as a membrane coupled to a radially inner circumferential part of the base portion 330 and may be optionally made of a material having a low thermal conductivity of, e.g., 5 W/(m·K). In this way, the radiation source 304 may be thermally decoupled from the holder 326, and, hence, from the gas to be analyzed.

In FIG. 5, the radial and axial directions are denoted by the reference characters R and A, respectively.

The source unit 324 may further include a collimator 322. The collimator 322 may include or may be configured as a Fresnel lens 323. The radiation source 304 may be positioned in or may overlap a focal point FP of the Fresnel lens 323. In this way, rays of electromagnetic radiation emitted by the radiation source 304 are parallelized by the Fresnel lens 323, i.e. converted into a beam of parallel electromagnetic radiation rays. The parallelized radiation beam is denoted by the reference character P.

The collimator 322 may further have an optical axis OA intersecting the collimator 322 and/or the radiation source 304.

The collimator 322 may be coupled to an axial end surface of the base portion 330 of the holder 326 by means of a plurality of posts 336. The posts 336 may be coupled to the holder 326 and/or to the collimator 322 by gluing or by anodic bonding. Similar to the posts 236 of the source unit 224 shown in FIG. 2, the posts 336 of the source unit 324 shown in FIG. 5 may be equipped with a reflector 337 at an outer surface thereof. In this way, a source unit 324 with a high electromagnetic radiation output may be provided.

The collimator 322 may be equipped with a collimator filter 329 in physical contact with a surface of the Fresnel lens 323 opposite to the radiation source 304.

As further shown in FIG. 5, the source unit 324 may be equipped with a source unit filter 328 provided on a side of the collimator 322 opposite to the radiation source 304. As shown in FIG. 5, the source unit filter 328 may include a plurality of layers 328a, 328b. In an exemplary embodiment, one of the layers 328a, 328b may be formed of $SiO_2$ and the respective other one of polycrystalline silicon. As set forth with respect to the source unit 224 shown in FIG. 2, a source unit filter 328 with defined filter characteristics may be provided by the layers.

The source unit filter 328 may be coupled to the collimator 322 by means of a plurality of posts 338 arranged on a radially outer portion of the source unit filter 328. The posts 338 may be coupled to the source unit filter 328 and/or to the collimator 322 by gluing or anodic bonding. The posts 338 supporting the source unit filter 328 may be equipped with a reflector 339 on an outer surface thereof configured to reflect electromagnetic radiation transmitted through the collimator 322.

The Fresnel lens 323 may be fabricated by etching a plurality of rings, e.g., of concentric rings, into a surface of a planar substrate made of a material transparent for the radiation emitted by the radiation source 104 such as of glass or plastic.

It should be noted that the present invention is not limited to the above-disclosed configurations of the collimator. Alternatively or additionally, the collimator may be configured as a plasmonic structure, an array of collimator lenses, a Fresnel lens structure with more than a single layer (trench) to increase the contrast, or hollow-core fibers.

In the following, various examples of the present disclosure will be described.

Example 1 is gas analyzer. The gas analyzer may include: a gas chamber configured to receive a gas to be analyzed therein, a radiation source configured to emit electromagnetic radiation into the gas chamber, the electromagnetic radiation being adapted to selectively excite gas molecules of a specific type that is to be detected in the gas received in the gas chamber, a collimator configured to collimate the electromagnetic radiation emitted by the radiation source, and a sensor configured to detect a physical quantity indicative of a degree of interaction between the electromagnetic radiation emitted by the radiation source and the gas to be analyzed.

In Example 2, the subject matter of Example 1 may optionally further include that the collimator has an optical axis. The radiation source may be positioned on the optical axis.

In Example 3, the subject matter of any one of Examples 1 or 2 may optionally further include that the optical axis intersects the collimator.

In Example 4, the subject matter of any one of Examples 1 to 3 can optionally further include that the collimator includes at least one of a group including: a convex lens, a concave mirror, a Bragg reflector, and a Fresnel lens.

In Example 5, the subject matter of Example 4 can optionally further include that the collimator is configured as a concave mirror having a reflectance in the infrared and/or in the visible and/or in the ultraviolet frequency range of at least 20%, or of at least 50%, or of at least 80%.

In Example 6, the subject matter of any one of Examples 1 to 5 can optionally further include that the collimator has at least one focal point. The radiation source may be positioned in a focal point of the collimator.

In Example 7, the subject matter of any one of Examples 1 to 6 can optionally further include a filter configured to selectively transmit electromagnetic radiation emitted by the radiation source.

In Example 8, the subject matter of Example 7 can optionally further include that the filter is configured as a tunable filter the transmission characteristics of which are tunable.

In Example 9, the subject matter of Example 8 can optionally further include that the tunable filter includes or is configured as a plasmonic filter and/or a Fabry-Pérot interferometer.

In Example 10, the subject matter of any one of Examples 7 to 9 can optionally further include that the filter includes or is configured as a collimator filter in physical contact with the collimator.

In Example 11, the subject matter of Example 10 can optionally further include that the collimator filter is configured as a filter layer deposited on a surface of the collimator.

In Example 12, the subject matter of any one of Examples 1 to 11 can optionally further include a source unit including a holder supporting the radiation source and/or the collimator. The source unit may be configured as a pre-assembled unit.

In Example 13, the subject matter of Examples 7 and 12 can optionally further include that the filter includes or is configured as a source unit filter separated from the collimator and supported by the holder.

In Example 14, the subject matter of any one of Examples 12 or 13 can optionally further include that the holder includes a substantially annular base portion and a plate-like carrier supporting the radiation source.

In Example 15, the subject matter of Example 14 can optionally further include that the carrier is made of a material having a thermal conductivity of less than 5 W/(m·K).

In Example 16, the subject matter of any one of Examples 14 or 15 can optionally further include that the carrier is configured to transmit electromagnetic radiation emitted by the radiation source.

In Example 17, the subject matter of Examples 13 and 16 can optionally further include that the carrier includes or is configured as a source unit filter.

In Example 18, the subject matter of any one of Examples 1 to 17 can optionally further include that the radiation source includes at least one of a group including: a black-body radiator, a photodiode, and a laser.

In Example 19, the subject matter of Example 18 can optionally further include that the radiation source includes or is configured as a black-body radiator configured as an electrically heatable body.

In Example 20, the subject matter of any one of Examples 18 or 19 can optionally further include that the radiation source includes or is configured as a black-body radiator including a plurality of perforations.

In Example 21, the subject matter of any one of Examples 1 to 20 can optionally further include that the gas chamber is delimited by a reflector configured to reflect electromagnetic radiation emitted by the radiation source.

In Example 22, the subject matter of Example 21 can optionally further include that the reflector has a reflectance in the infrared and/or in the visible and/or in the ultraviolet frequency range of at least 20%, or of at least 50%, or of at least 80%.

In Example 23, the subject matter of any one of Examples 1 to 22 can optionally further include that the gas chamber is in permanent gas flow communication with the exterior of the gas analyzer.

In Example 24, the subject matter of any one of Examples 1 to 23 can optionally further include that the radiation source is configured to selectively excite gas molecules of a specific type that is to be detected in the gas received in the gas chamber in a time-varying fashion, thereby generating acoustic waves as the physical quantity indicative of the degree of interaction between the electromagnetic radiation emitted by the radiation source and gas molecules of the type that is to be detected in the gas received in the gas chamber. The sensor may include or may be configured as an acoustic-wave sensor adapted to detect acoustic waves generated by the electromagnetic radiation.

In Example 25, the subject matter of Example 24 can optionally further include that the sensor is positioned inside of the gas chamber.

In Example 26, the subject matter of Example 24 can optionally further include that the sensor is positioned in a reference-gas chamber gas-tightly separated from the gas chamber and filled with a reference gas containing a well-defined amount of gas molecules of the type that is to be detected in the gas chamber.

In Example 27, the subject matter of any one of Examples 1 to 26 can optionally further include that the sensor includes or is configured as an optical sensor adapted to detect electromagnetic radiation emitted by the radiation source.

Example 28 is a mobile device including a gas analyzer of any one of Examples 1 to 27.

In Example 29, the mobile device of Example 28 can be optionally configured as a mobile phone.

While the invention has been particularly shown and described with reference to specific embodiments, it should be understood by those skilled in the art that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

What is claimed is:

1. A gas analyzer, comprising:
   a gas chamber configured to receive a gas to be analyzed therein;
   a radiation source configured to emit electromagnetic radiation into the gas chamber, wherein the electromagnetic radiation is adapted to selectively excite gas molecules of a specific type that is to be detected in the gas received in the gas chamber, wherein the radiation source comprises a black-body radiator configured as an electrically heatable body;
   a collimator configured to collimate the electromagnetic radiation emitted by the radiation source, wherein the collimator comprises a concave mirror positioned on a side of the electrically heatable body opposite the gas chamber, wherein the electrically heatable body comprises at least one through-hole formed therein to allow electromagnetic radiation reflected by the concave mirror towards the gas chamber to pass therethrough;
   a plate-like carrier supporting the electrically heatable body and configured to transmit electromagnetic radiation emitted by the electrically heatable body towards the concave mirror; and
   a sensor configured to detect a physical quantity indicative of a degree of interaction between the electromagnetic radiation emitted by the radiation source and the gas to be analyzed.

2. The gas analyzer of claim 1,
   wherein the collimator has an optical axis, wherein the radiation source is positioned on the optical axis.

3. The gas analyzer of claim 2,
   wherein the optical axis intersects the collimator.

4. The gas analyzer of claim 1,
   wherein the collimator further comprises at least one of a group comprising: a convex lens, a Bragg reflector, and a Fresnel lens.

5. The gas analyzer of claim 1,
   wherein the concave mirror has a reflectance in the infrared and/or in the visible and/or in the ultraviolet frequency range of at least 20%, or of at least 50%, or of at least 80%.

6. The gas analyzer of claim 1,
   wherein the collimator has at least one focal point, wherein the radiation source is positioned in a focal point of the collimator.

7. The gas analyzer of claim 1,
   further comprising a filter configured to selectively transmit electromagnetic radiation emitted by the radiation source.

8. The gas analyzer of claim 7,
   wherein the filter is configured as a tunable filter the transmission characteristics of which are tunable.

9. The gas analyzer of claim 8,
   wherein the tunable filter comprises or is configured as a plasmonic filter and/or a Fabry-Pérot interferometer.

10. The gas analyzer of claim 7,
    wherein the filter comprises or is configured as a collimator filter in physical contact with the collimator.

11. The gas analyzer of claim 10,
wherein the collimator filter is configured as a filter layer deposited on a surface of the collimator.

12. The gas analyzer of claim 1,
further comprising a source unit comprising a holder supporting the radiation source and/or the collimator, wherein the source unit is configured as a pre-assembled unit.

13. The gas analyzer of claim 12,
further comprising a filter configured to selectively transmit electromagnetic radiation emitted by the radiation source, wherein the filter comprises or is configured as a source unit filter separated from the collimator and supported by the holder.

14. The gas analyzer of claim 12,
wherein the holder comprises a substantially annular base portion and the plate-like carrier supporting the radiation source.

15. The gas analyzer of claim 14,
wherein the carrier is made of a material having a thermal conductivity of less than 5 W/(m·K).

16. The gas analyzer of claim 1,
wherein the radiation source comprises at least one of a group comprising: a photodiode and a laser.

17. The gas analyzer of claim 1,
wherein the gas chamber is delimited by a reflector configured to reflect electromagnetic radiation emitted by the radiation source.

18. The gas analyzer of claim 17,
wherein the reflector has a reflectance in the infrared and/or in the visible and/or in the ultraviolet frequency range of at least 20%, or of at least 50%, or of at least 80%.

19. The gas analyzer of claim 1,
wherein the gas chamber is in permanent gas flow communication with the exterior of the gas analyzer.

20. The gas analyzer of claim 1,
wherein the radiation source is configured to selectively excite gas molecules of a specific type that is to be detected in the gas received in the gas chamber in a time-varying fashion, thereby generating acoustic waves as the physical quantity indicative of the degree of interaction between the electromagnetic radiation emitted by the radiation source and gas molecules of the type that is to be detected in the gas received in the gas chamber, wherein the sensor comprises or is configured as an acoustic-wave sensor adapted to detect acoustic waves generated by the electromagnetic radiation.

21. The gas analyzer of claim 20,
wherein the sensor is positioned inside of the gas chamber.

22. The gas analyzer of claim 20,
wherein the sensor is positioned in a reference-gas chamber gas-tightly separated from the gas chamber and filled with a reference gas containing a well-defined amount of gas molecules of the type that is to be detected in the gas chamber.

23. The gas analyzer of claim 1,
wherein the sensor comprises or is configured as an optical sensor adapted to detect electromagnetic radiation emitted by the radiation source.

* * * * *